US00PP30959P2

(12) United States Plant Patent
Hansen

(10) Patent No.: US PP30,959 P2
(45) Date of Patent: Oct. 22, 2019

(54) *BAPTISIA* PLANT NAMED 'DARK CHOCOLATE'

(50) Latin Name: ***Baptisia* hybrid**
Varietal Denomination: Dark Chocolate

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,479

(22) Filed: Nov. 20, 2018

(51) Int. Cl.
*A01H 5/02* (2018.01)
*A01H 6/54* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden

(57) ABSTRACT

A new and distinct plant cultivar of hardy herbaceous false indigo named *Baptisia* 'Dark Chocolate' characterized by chocolatey purple flowers on very long spikes maintaining their coloration from bud to anthesis. The new plant has an upright, short, mounded, multi-stemmed, winter-hardy habit with glaucous medium-green tri-foliate foliage and is suitable for landscaping as a specimen or en masse.

1 Drawing Sheet

Botanical classification: *Baptisia* hybrid.
Cultivar designation: 'Dark Chocolate'.

STATEMENT REGARDING PRIOR DISCLOSURES UNDER 37 CFR 1.77(B)(6)

The first public disclosure of the claimed plant, in the form of a sale, was made by Walters Gardens, Inc. on May 7, 2018. Prior to that, on Dec. 1, 2017 the claimed plant was displayed with a photograph and brief sales promotion on the website of Walters Gardens, Inc., who obtained the plant and all information relating thereto, from the inventor. No plants of *Baptisia* 'Dark Chocolate' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Dark Chocolate' and will be referred to hereafter by its cultivar name, 'Dark Chocolate'. The new cultivar represents a new false indigo, a hardy herbaceous perennial grown for landscape and cut flower use.

The new invention arose from an ongoing breeding program of the inventor at a nursery in Waseca, Minn. with continued evaluation at a wholesale perennial nursery in Zeeland, Mich. with the specific intention of improving garden worthiness of perennial false indigo plants with a wider variety of flower colors and improved garden habit.

*Baptisia* 'Dark Chocolate' was a single seedling selection from a cross from a pollination of a proprietary unreleased hybrid of *B. sphaerocarpa* x *B. alba* 'Yellow Hornet' (not patented) as the female or seed parent, and the male parent is a *Baptisia minor* selection (not patented).

Seeds were collected from the individual selected female plant in October of 2009 at the isolation block in Waseca, Minn., USA by the inventor. The seeds were sown by the inventor at a wholesale perennial nursery in Zeeland, Mich. in the fall of 2009 and the initial selection made in the spring of 2014 at the same nursery. Prior to being given the cultivar name 'Dark Chocolate' the new plant was assigned the breeder code of H9-10-02.

'Dark Chocolate' was initially asexually propagated by stem cuttings at a wholesale perennial nursery in Zeeland, Mich. in June of 2014. The resultant plants have demonstrated that the new plant remains stable and true to type in successive generations of asexual propagation.

The nearest comparison plants known to the inventor are 'Dutch Chocolate' U.S. Plant Pat. No. 23,872 and 'Brownie Points' U.S. Plant Pat. No. 26,624. 'Dutch Chocolate' has a fuller rounder habit with fewer branches per stems that are more spreading and less upright, and the flower spikes are much shorter. The flowers of 'Dutch Chocolate' are similar in color, but are smaller and more concealed in the foliage and effective for a shorter period. 'Brownie Points' is taller and broader in habit and the flowers open to a lighter, more butterscotch-colored and not as deeply-colored chocolatey-purple as the new plant and the flower spikes are much shorter. The female parent has yellow flowers on long spikes and the habit is vase-shaped. The male parent has violet-blue flowers on shorter spikes and the foliage is smaller.

The 'Dark Chocolate' differs from all *Baptisia* known to the inventor in the following combined traits:

1. Chocolate purple flowers on very long spikes.
2. Flowers maintain their chocolatey purple coloration from bud to anthesis.
3. Short, mounded, multi-stemmed, upright, winter-hardy habit.
4. Glaucous, medium-green, tri-foliate foliage.

BRIEF DESCRIPTION OF THE DRAWINGS

The photographs of the 'Dark Chocolate' demonstrate the unique traits of the new plant and the overall appearance.

The colors are as accurate as reasonably possible with color reproductions. Variation in ambient light spectrum, source and direction may cause the appearance of minor variation in color. The accompanying photograph is of an eight-year-old plant growing in an open, full-sun, trial garden in Zeeland, Mich.

DETAILED BOTANICAL DESCRIPTION OF THE PLANT

Figure 1:
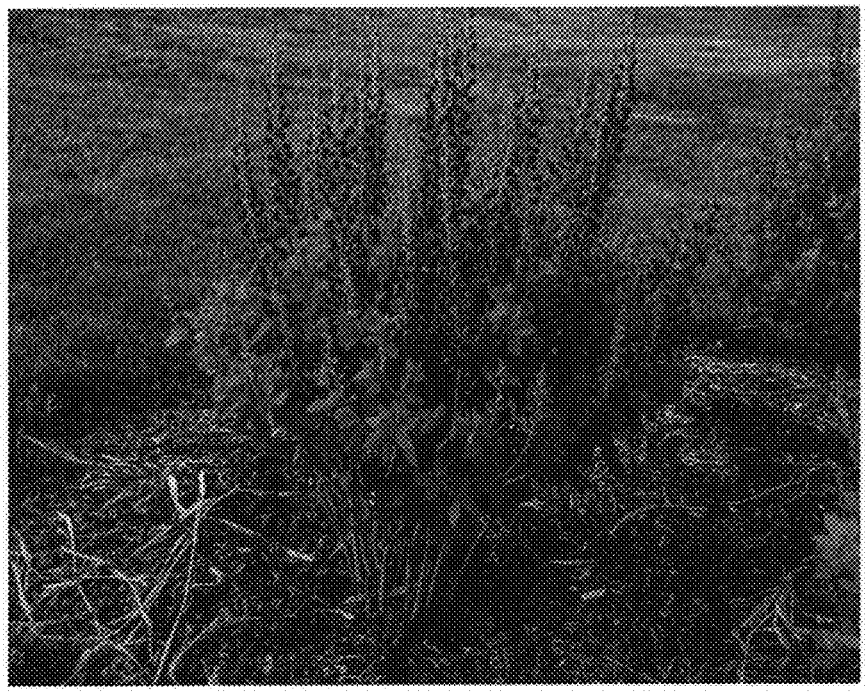
FIG. 1 shows the habit of a plant in full flower.
Figure 2:
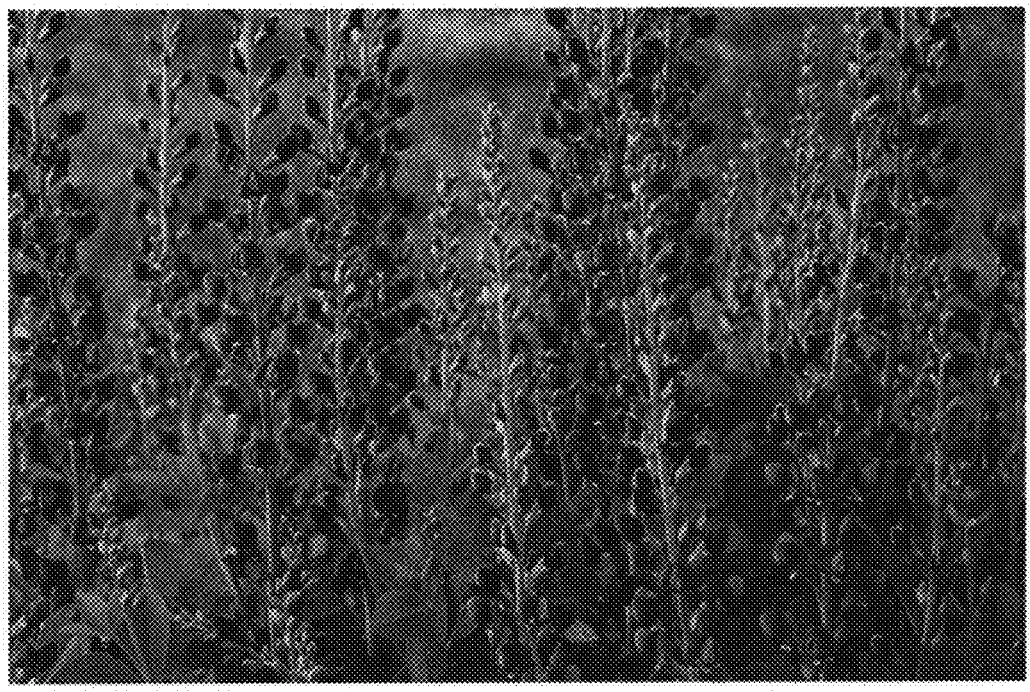
FIG. 2 shows a close-up of the flower scape.

The following is a detailed description of an eight-year-old plant of the new cultivar as grown outdoors in a full-sun trial plot at a wholesale nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, dense, well-branched, many-stemmed, broadly vase-shaped growth habit with long inflorescences held above the foliage;

Plant size: Stems and crown about 25.0 cm across at soil level, about 115 cm tall from soil to top of flowers and 118 cm wide just below initial flowers;

Roots: Fibrous, well-branched, long, deeply rooted;

Root color: Nearest RHS 161A;

Propagation method: Stem cuttings, rooting in about three weeks;

Growth rate: Moderate, similar to other *Baptisia;*

Stems: Rigid and upright to outwardly; highly glaucous; glabrous; cylindrical with longitudinal furrows; lower two to three nodes without leaves or branches; about 45 stems per plant; main stem to about 10.0 mm diameter at base and 115.0 cm tall to top of inflorescence, average about 108.0 cm long and about 10.0 mm diameter; normally about four alternately-arranged primary branches at about 60 degree angle above horizontal, up to 55.0 cm long and 5.0 mm diameter, average for primary branches about 48.0 cm long and 3.5 mm diameter, smaller distally;

Stem color: Base nearest RHS N138A;

Stem scales: At stem nodes; slightly glaucous; dehiscing to leave behind thin scar; about 4.4 cm long and 12.0 mm wide at base and 22.0 mm wide in center; frequently with apical three leaflets about 7.0 mm long and 2.0 mm wide in center of retuse apex with sharply pointed sides; truncate clasping base;

Stem scale color: Adaxial and abaxial margins nearest RHS 146B and centers nearest RHS 146D before dehiscing, and nearest RHS N200A after dehiscing;

Internodes: Eight on main stem to below flowers, eleven on primary branches to flowers; up to 9.0 cm apart between middle and upper nodes, average about 7.8 cm on main stem and primary branches;

Foliage: Alternate; ternate to palmately compound with three leaflets; outer two leaflets at about 65 to 80 degree angle to middle leaflet, increasing with leaf age; average about 7.0 cm long and about 7.5 cm wide, decreasing distally;

Leaflets: Three, oblanceolate; apex acute, base attenuate; margins entire; petiolate; adaxial surface matte, abaxial scaberulose; center leaflet average about 7.0 cm long and 2.5 cm wide; side leaflets average about 4.8 cm long and about 2.0 cm wide;

Leaflet color: Newly expanding adaxial nearest RHS 146B and abaxial nearest RHS 146B; mature adaxial nearest RHS 137A and abaxial nearest RHS 137B;

Venation: Pinnate, glabrous, thin, not conspicuous;

Vein color: Abaxial midrib basal one-third nearest RHS 145B, remaining abaxial veins and adaxial veins same color as surrounding leaf;

Petioles: Glabrous; slightly glaucous; flattened; up to about 3.0 cm long and 2.0 mm wide at base;

Petiole color: Adaxial nearest RHS 146B, abaxial nearest RHS 146C;

Stipules: Narrowly lanceolate to trifurcate, acute apex with base truncate and clasping stem; average about 32.0 mm long and 12.0 mm wide at base and 15.0 mm wide in middle; side lobes 11.0 mm long and 6.5 mm wide at base, center lobe about 5.0 mm long and 2.0 mm wide at base; with largest stipules below primary branches and decreasing distally and on secondary branches;

Stipule color: Nearest RHS 138A both surfaces;

Inflorescence: Main stem to about 71.5 cm long and 6.0 cm wide; average about 55.0 cm long and 6.0 cm wide; secondary branches to about 24.0 cm long and average about 21.0 cm long;

Flower: Zygomorphic, papilionaceous, non-secund, held at about 45 degree angle above horizontal when open; to about 80 flowers per main raceme and about 28 per secondary branch, average about 65 flowers per main raceme and 20 flowers per secondary branch; seasonally effective for about 3 to 4 weeks beginning in late May in Zeeland, Mich.; individual flower remain effective and on raceme for about four days; individually about 26.0 mm long, 18.0 mm tall and 16.0 mm wide at tallest and widest portions; an upper banner, a lower keel made up of two lobes folded around gynoecium and androecium; and two lateral wings or alae laterally appressed against keel;

Flower fragrance: None detected;

Peduncle: Terete with vertical ridges and furrows; glaucous; glabrous; from first flower to apex to about 71.5 cm long; diameter at the base of first flower about 5.0 mm and about 2 mm diameter at the apex;

Peduncle color: Blend between RHS 145A and RHS 146D;

Pedicel: Terete, glabrous, slightly glaucous; about 9.0 mm long and 1.0 mm diameter, decreasing in length distally; angle upwardly to slightly outwardly 70° above horizontal;

Pedicel color: Nearest RHS 147C;

Calyx: Campanulate; glaucous; glabrous abaxial and basal adaxial, lanulose in distal adaxial 3.0 mm; five sepals fused in basal 7.0 mm with acute apices; about 11.0 mm long and 12.0 mm across;

Sepals: Five; fused in basal 7.0 mm, acute apices; margins entire, micro-ciliolate; distal two lobes only dissected about 2.0 mm and side and lower lobes dissected about 4.0 mm deep; distal sepals about 2.5 mm wide at fusion; side and proximal sepals about 3.0 mm wide at fusion; side sepals reflexed, distal and proximal sepals adpressed to corolla; persists after petal drop;

Sepal color: Adaxial nearest RHS 144A; abaxial nearest RHS 146D;

Buds one day prior to anthesis: Oblong ellipsoid; flatted vertically; about 24.0 mm long and 9.0 mm tall and 6.5 mm wide near middle;

Bud color: About one day prior to opening nearest RHS 1C proximally where exposed by calyx and between RHS N186A and RHS N92A distally;

Petals: Five; with a lower fused keel, an upper banner, and two lateral wings or alae; keel comprised of two sections that are folded around stamens and pistil;

*Banner petal*.—Glabrous; conduplicate; curved upward and backward and furrowed in the longitudinal center; apex retuse; base claw; margin entire; about 22.0 mm long; 16.0 mm wide natural and 22.0 mm wide if flattened; claw-like base 5.0 mm long and narrowing to 2.0 mm at base and expanding to 4.0 mm wide before blade; color adaxial blade toward perimeter nearest RHS N186A, claw and basal blade nearest RHS 1B and furrow nearest RHS N144A; abaxial blade nearest RHS N186A, claw nearest RHS 151D.

*Keel*.—Comprised of two main lobes that are folded around stamens and pistil; fused about 4.0 mm from rounded apex; base auriculate; claw curved slightly upward, about 7.0 mm long and 1.0 mm across at base; overall about 22.0 mm long with blade 9.0 mm across near middle; color abaxial blade and claw nearest RHS 1C, abaxial blade margin strongly blushed with RHS N186A; adaxial between RHS 1B and RHS 1C, claw nearest RHS 1D, apex blushed lightly with RHS N186A.

*Alae*.—Two, enveloping keel; papilionaceous corolla appendage with rounded apex and claw-like base; apex rounded; blade base auriculate; claw base curved upwardly, claw about 7.0 mm long and 1.0 mm across at base; blade about 19.0 mm long and 9.0 mm wide in middle; total alae length with claw 23.0 mm long; with 2.0 mm lobe pointing toward base and about one-third of the way from base; alae adaxial distal three-quarters blade color nearest RHS N92A, basal one-quarter nearest RHS 2C, adaxial claw nearest RHS 1C; abaxial distal three-quarters blade color between RHS N186A and RHS N92A, basal one-quarter nearest RHS 1B, claw nearest RHS 1C.

Receptacle: Disk-shaped, about 3.0 mm diameter and 1.5 mm depth; color nearest RHS 138A;

Gynoecium: One, with superior ovary;

*Pistil*.—Stalked; glabrous; about 22.0 mm long.

*Style*.—Terete; tapering, narrowing distally; about 10.0 mm long and less than 1.0 mm diameter; color nearest between RHS 145B and RHS 145C.

*Stigma*.—Less than 0.5 mm diameter; color nearest RHS 155A.

*Ovary*.—Superior suspended by stipe; terete; about 5.0 mm long and about 1.5 mm in diameter; color nearest RHS 145C.

*Stipe*.—Terete; about 4.0 mm long and 0.7 mm diameter; color nearest RHS 145A.

Androecium:

*Stamens*.—Ten; enclosed within keel; not united; curved slightly upwardly; to about 23.0 mm long and 1.0 mm diameter.

*Filament*.—Terete; to about 22.0 mm long and about 1.0 mm in diameter; color nearest RHS 1D.

*Anther*.—Basifixed; longitudinal; ellipsoidal; about 2.0 mm long and 1.2 mm wide; color nearest RHS 17A.

*Pollen*.—Spherical; abundant; color nearest RHS 17A.

Fruit: Bivalve inflated pod; glabrous; ellipsoidal; with rounded based, apex rounded with beak; to about 28.0 mm long, 16.0 mm across and 21.0 mm tall, with thin linear terminal beak about 10.0 mm long and about 0.7 mm thick at base; average about 20.0 mm long, 14.0 mm across and 17.0 mm tall with beak 6.0 mm long and 0.5 mm thick at base;

Fruit color: Between N200A and RHS 202A;

Seeds: Average about 12 per flower (open pollinated); reniform; surface glabrous; about 4.5 mm long, 3.0 mm across and 1.5 mm thick; color nearest RHS 165A;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed;

It is claimed:

1. A new and distinct plant cultivar of hardy herbaceous false indigo named *Baptisia* 'Dark Chocolate' as herein described and illustrated.

* * * * *